United States Patent [19]

McNeely

[11] 4,248,597
[45] Feb. 3, 1981

[54] TIME WATCH OR DEPLETION INDICATOR FOR REMOVABLE SUBSTANCES

[75] Inventor: Gerald W. McNeely, Arden, N.C.

[73] Assignee: Akzona Incorporated, Asheville, N.C.

[21] Appl. No.: 968,871

[22] Filed: Dec. 12, 1978

[51] Int. Cl.³ .................................................. G01N 21/06
[52] U.S. Cl. ................................... 23/230 R; 116/206; 422/56; 422/58; 422/119
[58] Field of Search ........................ 422/58, 55–57, 422/59, 119, 60, 61; 23/230 R; 116/206

[56] References Cited

U.S. PATENT DOCUMENTS

| | | | |
|---|---|---|---|
| 3,681,027 | 8/1972 | Smith | 422/55 X |
| 3,966,414 | 6/1976 | Khattah et al. | 422/119 |
| 4,042,336 | 8/1977 | Larsson | 422/119 |
| 4,062,649 | 12/1977 | Kuderna et al. | 422/119 X |
| 4,066,403 | 1/1978 | Braschi | 422/57 |
| 4,126,417 | 11/1978 | Edwards | 23/230 R |
| 4,137,049 | 1/1979 | Couch et al. | 422/58 X |
| 4,195,055 | 3/1980 | Patel | 422/56 |
| 4,195,056 | 3/1980 | Patel | 422/56 |
| 4,195,057 | 3/1980 | Patel | 422/56 |
| 4,195,058 | 3/1980 | Patel | 422/56 |

*Primary Examiner*—Michael S. Marcus
*Attorney, Agent, or Firm*—Robert H. Falk; Charles A. Wendel; Francis W. Young

[57] ABSTRACT

A novel depletion indicator (time watch) for removable substances containing acid or basic groups is disclosed, together with a novel method of use therefor. The removable substance of a predetermined concentration comes into contact with a suitable pH color indicator that can change color at a predetermined pH range within a much larger measurable pH range, which color change occurs as the concentration of the removable substance diminishes by passing through a permeable film containing both the removable substance and the pH color indicator. The color change occurs at a predetermined time, e.g., the same time that the active ingredient has diminished to the point it is determined to be inactive.

30 Claims, 5 Drawing Figures

TIME WATCH OR DEPLETION INDICATOR FOR REMOVABLE SUBSTANCES

RELATED APPLICATIONS

This application is related by subject matter to Ser. No. 795,582 to Thomas Wayne Couch et al "DEVICE FOR USE AS AN ELAPSED TIME INDICATOR OR TIME TEMPERATURE INDICATOR", filed May 10, 1977, now U.S. Pat. No. 4,137,049, and (2) Ser. No. 919,005 to Robert L. Lilly et al "IMPROVED ELAPSED TIME INDICATOR", filed June 29, 1978, both incorporated by reference in full herein.

BACKGROUND OF THE INVENTION

1. Field of the Invention

The present invention relates to the field of organic chemistry, chemical compositions thereof, and devices therefor employed as time watches, and depletion indicators for pesticides and insecticides.

2. State of the Art

Many devices are known that can be used for attachment to an animal such as a dog, cat, or cow and that contain an active ingredient that is controllably released to protect the animal against various parasites, insects, bacteria, and the like. These devices often have a useful life of from three to eight months, but there is no present way of determining in a simple, economical, and ready manner when the effectiveness of the active ingredient in the controlled release formulation has expired. Moreover, it is strongly desired by those in the art to employ a depletion indicator time watch that would be physically and chemically independent from the device ("parent device") for which depletion is to be measured, because (1) it would be sometimes convenient to watch the depletion indicator remote from the parent device, and (2) the active substance most often contains toxic substances for which it is further desirable to utilize a depletion indicator not containing toxic substances, for readily apparent safety reasons. The parent device most often contains a volatile controlled-release substance, which upon activation of the active substance is depleted or removed at a known predetermined rate.

It is known from U.S. Pat. No. 4,062,649 to Kuderna, issued Dec. 13, 1977, that the effective life of a controlled release formulation containing a volatile phosphate ester pesticide can be visually determined by using a mixture of an inorganic base which reacts with the ester, which comprises a suitable color-change indicator for acid/base reactions, an inert absorbent carrier, and a humectant. This mixture will contact a proportion of the pesticide vapor emitted therefrom. The amount of the base in the mixture is predetermined and directly related to the effective life of the formulation. The base is a necessary component of the mixture because it is required to react with the acid ester. When the indicator changes color to that of its neutral or basic form, the change signals the end of the effective life of the pesticide. It is necessary that a reaction take place between the ester and the inorganic base to form the corresponding salts during the course of operation of this visual indicator. However, Kuderna's device is both physically and chemically dependent on the parent device.

3. Description of the Prior Art

The prior art is perhaps best exemplified by German Offenlengungsschrift No. 2,519,126, which discloses an insecticidal device to be placed around the neck of a domestic animal, comprising:
  (a) "Diazinon" and/or "Diazoxon" as an active ingredient;
  (b) a macromolecular vinyl or vinylidene compound;
  (c) a plasticiser;
  (d) optionally, a dye, a pigment, a stabilizer and a deodorant; and
  (e) optionally, a container Normally, one would expect from the teachings of the art, including Kuderna et al above, that both an acid and base are needed to utilize a pH color indicator for an indicator for a pet collar. Surprisingly, I have found this not to be the case.

SUMMARY OF THE INVENTION

A novel device is disclosed for indicating the depletion of a removable substance, i.e., a controlled release formulation, comprising:
  (a) a porous matrix containing (1) the removable substance, which substance has acidic or basic groups in a predetermined amount, and is capable of diffusing through a permeable film, and (2) a suitable pH color indicator that undergoes a color change at a predetermined pH range within a broader pH range, which broader pH range is bounded by one pH measurable at said predetermined amount when said removable substance commences to diminish through said permeable film, and a second pH measurable after the removable substance has diffused through a said permeable film and the color change has occurred; and
  (b) a container comprised of said permeable film, containing said porous matrix (a).

The porous matrix is preferably selected from the group consisting of celluose, polystyrene, Teflon (a tetrafluoroethylene polymer of duPont de Nemours and Company), and polyester. The suitable pH indicator is preferably selected from the group consisting of methyl red, chlorophenol red, ethyl red, malachite green, and phenol red, which are to be combined with acids or from the group consisting of o-cresol-phthalein, thymolphthalein, alizarin yellow and phenolphthalein, which are to be combined with bases. The permeable film is preferably selected from the group consisting of polypropylene, polyethylene, polyvinyl chloride, polycarbonate, polyester and polyamide, and is most preferably polyvinyl chloride. Preferable combinations of release substance and suitable pH color indicator are, respectfully (1) 2,2-dichlorovinyl dimethyl phosphate and chlorophenol red; (2) hydrochloric acid and methyl red; (3) dimethyl phosphate and chlorophenol red; and (4) hydrochloric acid and malachite green. The removable substance may be a pesticide or insecticide, generally the same formula as the active substance in the parent device, but is preferably a non-toxic device.

A time watch is also disclosed for determining when a predetermined period of time has elapsed comprising:
  (a) a porous matrix containing (1) an acid or a base, and (2) a suitable pH color indicator that undergoes a color change at a predetermined pH within a broader pH range, which broader pH range is bounded by (aa) a pH of (a)(1) measurable before a selected controlled release substance having acidic or basic groups and diffusable through a permeable film contacts (a)(1), with the proviso that if (a)(1) is an acid, the groups are basic, and if (a)(1) is a base, the groups are acidic; and
  (b) an impermeable crushable pouch containing said controlled release substance with the proviso that the porous matrix and said pouch are separated by said permeable film through which the controlled release substance is diffusable; and (c) a transparent impermeable container containing (a) and (b) by which the porous matrix can be observed.

Other variations of the aforesaid three components are possible: one may choose acid or base in the matrix, the permeable film, and the controlled release substance so that (a)(1) migrates from the matrix through the film to the pouch or base causing a color change, i.e., (a)(1) becomes a release substance. Or, for short periods of time the acid or base of (a)(1) can be omitted. Still further, one may place the controlled release substance in the matrix and place a removable substance therein having acid or basic groups therein, and utilize the crushable pouch as an area from which the controlled release substance may diffuse. For each of these devices, one merely squeezes the crushable pouch until it collapses, so that the removable substance may commence moving through the permeable film.

It is an object of the present invention to provide a depletion indicator for removable or controlled release formations.

It is another object of this invention to provide a depletion indicator for removable or controlled release formulations using a minimum number of components.

It is a further object of the present invention to provide a simple depletion indicator for a removable or a controlled release formulation for use in pet collars and the like.

It is yet another object of this invention to provide a depletion indicator based upon a removable substance containing acid or basic groups and a suitable pH color indicator that changes color within a predetermined pH range that occurs as the concentration of the removable substance diminishes by passing through a permeable film without involving a chemical reaction dependent upon the parent device for which it is to monitor.

It is another object of the invention to provide a depletion indicator or time watch which is chemically and physically independent from the parent device of which it is to monitor.

It is a further object of the present invention to produce a time watch based upon a removable substance containing acid or basic groups in a crushable pouch and a suitable pH indicator and an acid or base in a matrix, wherein the indicator changes color in a predetermined time within a predetermined pH range, which color change occurs as the concentration of the removable substance in the pouch diminishes by passing through a permeable film after the pouch is crushed.

DESCRIPTION OF THE PREFERRED EMBODIMENTS

The present invention relates in one embodiment to a porous matrix containing (1) a removable substance that has either an acid or basic group and (2) a suitable pH color indicator. As the substance passes from the matrix via a permeable film, the pH therein will change due to a decrease in the concentration in the removable substance, and at a certain predetermined pH, the pH color indicator selected will change color, indicating that the removable substance is no longer present in what is determined beforehand to correlate an effective amount of an active ingredient (e.g., a pesticide or insecticide) of a parent device (e.g., a pet or animal collar).

The type of removable substances having an acidic or basic group can, of course vary depending upon the objects of the invention and the particular circumstances. For use in a pet collar, among suitable acid group-containing substances are the same phosphate ester pesticides now commonly used in pet collars having the formula:

wherein each R is alkyl from 1 to 4 carbon atoms, R' is hydrogen, chlorine or bromine, hal is chlorine or bromine, and X is oxygen or sulphur as disclosed in U.S. Pat. No. 4,062,649, incorporated herein. These compounds can be readily used because they are also volatile. On the other hand, the novel devices of my invention, both depletion and time watch indicators, need not employ a toxic material as its removable substance, but preferably may employ a non-toxic substance, such as a mineral acid or amine base also chemically and physically independent of the pet collar or other device being monitored. Hence, the novel monitor may be in one location, and the device being monitored may be in a different location. Also, the indicator will be comprised of non-toxic materials. In the case of a flea collar, it will mean a reduced chance of harm to pets and children who might chew on the indicator. Other phosphorous containing materials useful in such devices are disclosed, particularly in German Offenlengungsschrift No. 2,519,126 of Nov. 20, 1975, French Patent Application No. 2,057,092, French Patent Application No. 2,117,769, and French Pat. No. 1,603,822, all incorporated herein. In the alternative, a mineral acid such as HCl is employed (from about 0.1 N to about 10 N depending on the suitable indicator selected). Other phosphorus containing materials and other pesticides and insecticides are disclosed in U.S. Pat. Nos. 3,318,769; 3,608,062; 3,295,246; 3,605,321; 3,213,830; 2,431,924; 2,958,469; 3,844,718; 2,956,073; 3,116,201; 3,111,539; 3,102,842; 3,295,246; 3,551,192; 2,431,924; and 1,535,536; see also British Patent Specification No. 1,420,186 (pet collar); and German Offenlegungsschrift No. 2,403,951 all incorporated herein.

It is also possible to use solid pesticides in dust or powder form as long as they contain acid or basic groups. As the concentration of the substance diminishes by passing through the permeable film of the flea collar indicator, the change in pH will activate a suitable pH color indicator in contact with the remaining portion of the solid pesticide at a predetermined pH, signaling when the pesticide in the parent device (flea collar) is no longer present in what is determined to be an effective amount.

Any inorganic or organic substance containing either an acid or a basic group can be used for the removable substance in the invention as long as it is capable of passing through the selected permeable film layer, i.e., it is a controlled release substance. Some acid group containing substances include hydrochloric acid (generally 0.01 N to 10 N depending upon pH indicator), acetic acid, sulfuric acid, propionic acid, dimethyl phosphite, and glycolic acid. Suitable basic group containing substances include amines such as ethylene diamine and triethylamine, ammonia (concentrated ammonium hydroxide) and phosphines such as trimethylphosphine and triethylphosphine. Other active ingredients are readily apparent to those skilled in the art.

Among the many suitable pH indicators that may be used in the present invention according to the circumstances of the removable substances, permeable films, and solvents selected, are methyl red, chlorophenol red, ethyl red, malachite green, and phenol red for acids and o-cresolphthalein, thymolphthalein, alizarin yellow and phenolphthalein for bases. It is also possible under certain circumstances to use mixtures of these indicators.

For a two-component depletion indicator, one first chooses a removable inorganic or organic substance for the device to be monitored (parent device). This removable substance may be a pesticide or insecticide, as exists in the parent device or in the alternative; be a non-toxic substance. One then concentrates the substances, perhaps in a solvent, in an effective amount or concentration which is enough to monitor the parent device for a predetermined period of time (usually 3 to 6 months for pet collars), i.e., passes slowly enough through a selected permeable film so as to provide a slow change in pH over a large pH range.

One then determines the pH when the removable substance (1) commences to deplete ($pH_1$), and (2) when it is completely depleted ($pH_2$) and (3) when it is depleted as to correspond when the parent device has been rendered ineffective for the designed purpose ($pH_3$). Hence, a pH range is determined, with $pH_3$ being between $pH_1$ and $pH_2$. A suitable pH indicator is selected by one in the art which bridges $pH_3$, i.e., changes color in that portion of the pH range (between $pH_1$ and $pH_2$) wherein the parent device becomes ineffective to accomplish the desired purpose. Utilizing this methodology, some moderate amount of experimentation time length that the parent device is active, and the permeable film, removable substance and pH color indicator chosen.

In a broader context it should be noted that any pH indicator listed in the *CRC Handbook of Chemistry and Physics*, 58th Edition, CRS Press Inc., Cleveland, Ohio or *Lange's Book of Chemistry*, 11th Edtion, McGraw-Hill Book Company, New York, N.Y., both incorporated herein, may be used as long as it is employed in combination with a proper acid or base containing removable substance in a suitable concentration. It is necessary as described above that the pH of the acidic or basic group-containing substance must pass through the color changing pH range of the pH indicator. See also (1) *H. J. CONN'S BIOLOGICAL STAINS*, 9th Edition 1977-edited R. D. Lillie, M.D.; The Williams & Wilkins Co., Baltimore, Md. publisher; (2) *COLOUR INDEX*, 3rd Edition, Society of Byers and Colourists, Bradford, Yorkshire, England, publishers (1971); (3) *MCB CHEMICAL REFERENCE MANUAL*, Table 176-177 (August 1977), MCB Manufacturing Chemists, Norwood, Ohio, publisher; and (4) Kodak publication No. JJ-13, "pH Ranges and Color change of Eastman Indicators", Eastman Kodak, Rochester, N.Y., all incorporated herein.

In another aspect of this invention, one, two or three component embodiments of the invention can be used as a time watch for the determination when a sterile item in a hospital or laboratory must be resterilized. The color change will indicate when a period of time has elapsed. This embodiment is shown in Example 9, infra.

It is especially preferred that the depletion indicator of the present invention be used for pet collars and the like. Under these conditions, it is preferred to place the acid or basic group-containing substance and the suitable pH indicator on a porous disc or matrix which in turn is placed in a permeable plastic film containing the treated disc with the entire operation can be used as a depletion indicator for a pet collar.

The porous disc or matrix can be any of a variety of materials including Teflon ®, polystyrene, polyester, cellulose, or the like, which is capable of containing the mixture of the suitable pH indicator and the acid or basic group-containing substance and is inert thereto.

The permeable film that can be used in the pet collar is preferably any film that is permeable to vapors and these include polypropylene, polyvinylchloride (pvc), polyethylene, polycarbonate, polyester, and polyamides. Most preferably the film is pvc. It is generally from 5 mils (0.005 inch) to 15 mils (0.015 mils) in thickness.

It is also possible to use one or more solvent(s) in the device of the present invention as long as the solvent(s) is (are) inert toward and miscible with the substance indicator mixture; and providing that the solvent(s) are (were) a liquid between temperatures in which the indicator is to be used, e.g., temperatures ranging from −25° to 125° F. for a pet collar the environment in which the collar is shipped and is used.

The ratio of the chemical to the suitable indicator depends upon the color depth and contrast desired by the individual user, the indicator employed, the concentration of the indicator and removable substance, and the predetermined period of time before color change and can be readily determined by one of ordinary skill in the art. An operable range is generally from about 1 $g/10^2$ ml to about 1 $g/10^6$ ml of indicator to substance. However, about 0.1 $g/10^2$ ml of suitable indicator to removable substance ordinarily gives very good color contrast in most cases for most indicators involving pet collars or provides a starting point for reasonable experimentation. In a particular preferred embodiment, the porous matrix containing a suitable acid base pH color indicator and a removable substance containing either an acid or basic group will be sealed inside a permeable film which is inside a crushable plastic (impermeable) film pouch. After the pouch is crushed, the removable substance diffuses out of the permeable film so that the pH of the device will slowly change at a predetermined rate and at a narrow preselected pH range, the suitable indicator changes color. By a combination of the proper porous matrix, pH color indicator, removable substance, and porous film, a device can be prepared so that the pH of the novel monitor device will be in the color changing range of the pH color indicator when the parent device being monitored (such as a pet collar containing an insecticide or pesticide) has just become ineffective. The selection of the variables of the thickness and porosity of the disc containing chemical, type of film used and thickness of the film are within the knowledge of one in the art.

Since pH indicators change colors over a range of one or more pH units, the slow diffusion of vapors out of the plastic pouch might result in a slow gradual color change in the device that extends over a few days to several weeks. Many pH indicators exist which have sharp or slow color changes for a specified pH.

In another embodiment, a reference color can be used if a more precise end point is desired by the user. Two types of reference color formulations can be used in carrying out the invention. One involves the use of a reference color which matches the end point color of the treated disc. This reference color can be painted on the device as a band, a semi-circle, a center dot or outer ring of the disc, strips that traverse the disc, or the like.

Another method of placing a reference color on the device consists of preparing a device containing two treated discs, one that turns the desired color in a short time period and a second disc having a color that matches the color of the first disc at the end of the desired period of time. It is also possible to use this same type of application on only one disc wherein two half discs are employed. One-half will turn the desired color in a short time and the second half will match the color at the end of the desired time. Both of these devices can be sealed in an impermeable pouch, preferably of heat sealed aluminum, that contains the same amount and type of chemical inside the device. With this type of packaging the contents of the device will remain the same (initial contents) until the device is removed from the pouch and put into use. Many other configurations are possible.

In yet another embodiment of the invention, a time watch can be prepared to indicate by a change in color when a given time period has elapsed using a three-component system. A porous disc or matrix is prepared containing a suitable pH indicator and either an acid or base. A crushable impermeable pouch contains a removable substance having acidic or basic groups depending upon the component added to the pH indicator in the porous disc. The removable substance has acidic groups if the disc contains a base, and visa versa. The pouch and the disc are separated by a vapor permeable film. Upon crushing the pouch, the removable substance slowly migrates through the permeable film to the disc, and the acid or base therein begins to be neutralized, and the pH starts to change. At a predetermined time later, the pH changes to a sufficient point that the color of the indicator changes. The impermeable crushable pouch is made from materials known to those in the time watch art, such as a fragile crystalline polymer such as polycarbonate or polyethylene, plastic, glass (8 mils) or acrylonitrile/butadiene/styrene ("ABS" 1 to 2 mils), or polybutylene and is generally onion skin in thickness unless otherwise stated above so as to be easily collapsible upon crushing of the pouch by the fingers. It may be dipped in wax to insure impermeability. In the three-component system, the disc and pouch are contained in an impermeable film of 0.010 to 0.015 inch thickness. The permeable film between the pouch and matrix has a thickness generally to 0.001 to 0.005 inch depending on the time before it is desired for the pH indicator to change color and the indicator, acid or base, and removable substance chosen.

The following examples are employed to show the usefulness of the instantly claimed invention.

EXAMPLE I

This example shows how the color of chlorophenol red and "Vapona TM " by Shell Oil Company, Houston, Tex. (2,2-dichlorovinyl dimethyl phosphate) was determined.

Small strips of "Porex TM " (a porous polypropylene material available from the Glassrock Co., Atlanta, Ga.) of 1/32 to ⅛ inch thickness and generally of 1/16 inch thickness were dipped in a solution of 0.1 g chlorophenol red and 10 ml acetone and then dried in a fume hood. The resulting red colored strips were dipped in liquid "Vapona TM ", a 2,2-dichlorovinyl dimethyl phosphate, volatile pesticide containing an acid group, and the strips turned to an off-white color. One of the off-white colored strips was heated to approximately 100° C. under reduced pressure, the color of the strip in the oven turned back from off-white to red. After several days, the same color change took place in the strip placed in the fume hood.

EXAMPLE 2

This example was undertaken to determine the color of solutions of isopropyl alcohol containing phenolphthalein and ethylene diamine, a base.

Phenolphthalein 0.1 g was dissolved in an aqueous solution of 5 ml of 80% isopropyl alcohol and 5 ml ethylene diamine and a violet color solution was obtained. A piece of white polypropylene was allowed to soak in the solution for several minutes. The excess solution was removed from the violet colored strip with a paper towel. This colored strip was then cut into two pieces and one piece was placed in an oven at 120° C., while the other piece was exposed to the atmosphere at room temperature. After approximately 10 minutes of heating at 120° C. in the oven, the piece turned white. The second piece also turned white after being exposed to the atmosphere overnight.

EXAMPLE 3

This example reports the determination of the color of solutions of isopropyl alcohol containing methyl red and hydrochloric acid.

A piece of white polypropylene was soaked for several minutes in a 5 ml aqueous 50% isopropyl alcohol solution of 0.1 g methyl red also containing 5 ml of 10 N hydrochloric acid. The excess solution was removed from the red colored strip with a paper towel and the strip was then cut into two pieces. One piece was put into an oven at 110° C. and the other piece was exposed to the atmosphere at room temperature. After approximately 10 minutes of heating at 110° C., the piece in the oven had changed color from red to cream. A comparable color change took place in the piece exposed to the atmosphere at room temperature after overnight exposure.

EXAMPLE 4

This example illustrates the color change of a "Vapona TM "/chlorophenol red system as "Vapona TM " diffused out of a envelope made of polypropylene film.

A small porous polypropylene disc containing about 0.07 g of a 10 ml "Vapona TM " solution containing 0.1 g chlorophenol red was heat sealed between two layers of 5.0 mil (0.005 inch) thick polypropylene film. The device was placed in a fume hood and observed for color change of the disc as the "Vapona TM" diffused through the film. After several days the off-white disc had turned to a pink color which slowly turned red over the next 70 to 90 days.

EXAMPLE 5

This example illustrates the color change in a "Vapona TM"/chlorophenol red system as "Vapona TM" diffuses out of a polyvinylchloride (pvc) pouch.

In a manner similar to that of Example 4, a disc containing "Vapona TM" and chlorophenol red was placed and heat-sealed between two layers of polyvinylchoride (pvc) film having a thickness of 7.5 mils. Similar results occurred in this embodiment.

EXAMPLE 6

This example shows the color change in a hydrochloric acid/chlorophenol red system as the HCl diffuses out of a 5.0 mil polypropylene envelope.

A small porous polypropylene disc is treated with about 0.07 g of a solution prepared by dissolving 0.1 g of chlorophenol red in a mixture of 10 ml of 0.1 N hydrochloric acid and 10 ml of Formula 30, a mixture of 90% of 95% ethanol denatured with methanol to form an azeotropic mixture. The resulting yellow colored disc was heat sealed between two layers of 5.0 mil thick polypropylene film and the resulting assembly placed in an oven at about 60° C. The pressure in the oven was reduced and the assembly observed for color changes as the HCl diffused through the film. After a few hours in the oven, the yellow color had become reddish orange and after a few days, the color had turned to a maroon red.

EXAMPLE 7

This example shows the determination of color change in a hydrochloric acid/malachite green system as the hydrochloric acid diffused out of a polypropylene envelope of 5.0 mil thickness.

A configuration similar to that of Example 6 was prepared except that the solution consisted of malachite green dissolved in equal volumes of 10 N HCl and Formula 30. The disc changed from a yellow to a dark green color upon exposure to the atmosphere and as the HCl diffused out of the pouch.

EXAMPLE 8

This example shows the determination of color change in a dimethyl phosphite/chlorophenol red system as dimethyl phosphite diffused from a polypropylene pouch.

A small porous polypropylene disc containing about 0.07 g of a 10 ml dimethyl phosphite solution containing 0.1 g chlorophenol red was heat sealed between two layers of polypropylene film (each layer 5.0 mil thick). The resulting assembly was placed in an oven under reduced pressure at about 60° C. After a few hours the color of the disc had turned from light yellow to pink. The next several days established a color change from pink to red.

EXAMPLE 9

This example shows the preparation and use of a time watch indicator.

A small disc of Whatman filter paper is treated with a solution containing 0.1 g thymol-blue dissolved in 10 ml of a 50—50 methanol-water solution. The resulting yellow-colored disc was then heat sealed between two layers of polyethylene film. A second filter paper disc was treated with concentrated hydrochloric acid and heat sealed between a 1.0 mil layer of polyethylene film of the layers into which the yellow-colored disc had been heat sealed and another layer of polyethylene film. After standing at room temperature for about 36 hours, the yellow-colored disc had turned to violet.

EXAMPLE 10

Figure 1:
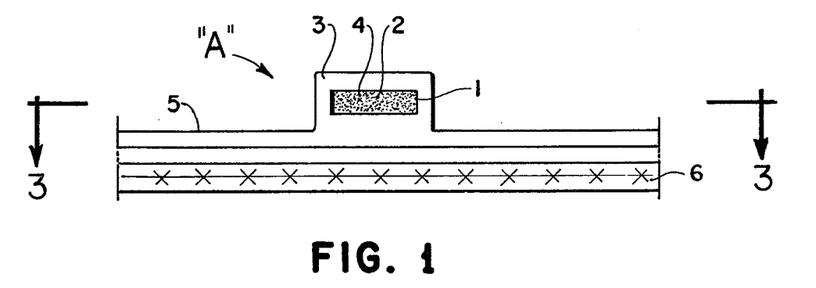
In FIG. 1 an embodiment of the two-component depletion indicator for a pet collar is shown from a horizontal cut-away viewpoint (Example 10).

In FIG. 1 an embodiment for the novel depletion device (pet collar indicator) of my invention is shown from horizontal cut-away viewpoint. The indicator has been activated in FIG. 1. The embodiment takes the form of a cavity "A" protruding from band 5 which encircles a pet collar 6 (e.g. such as Hartz's "2-in-1" TM Flea and Tick Collar, Hartz Mountain Co., Harrison, N. J. or "Sargeant's Sentry" TM Flea and Tick Collar, Miller-Morton Co., Richmond, Va.). The cavity "A" comprises a transparent permeable film 3, preferably of polypropylene or polyvinyl chloride, and preferably of from 5 to 15 mils thickness which surrounds and makes visible a matrix 1 containing the suitable pH color indicator 4 and the removable substance 2. The pH color indicator 4 and removable substance 2 are so chosen that after the indicator has been activated, a color change will result after a predetermined period of time signaling when the active substance in a pet collar 6 has depleted to the point that it is ineffective (hence, the cavity "A" and band 5 need not be physically adjacent to the collar 6). Preferable pairs of releasable substances and pH color indicators are HCl from about 0.01 N to about 0.1 N with methyl red, and HCl concentration of 1 N to 10 N with malachite green; the amount of HCl is dependant upon the estimated time for which the pet collar is effective. In this manner a non-toxic material, HCl, is employed to determine the depletion of the pet collar, which contains a toxic material such as "Vapona TM", or 2,2-dichlorovinyl dimethyl phosphate. Of course, one may employ the same removable substance as is in the pet collar for the novel depletion indicator.

Figure 2:
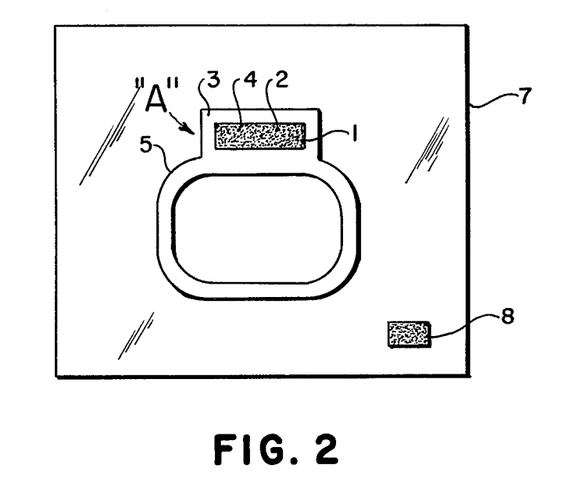
FIG. 2 shows the same embodiment as FIG. 1 from the same viewpoint, but omitting the proximity of the pet collar, and with the pet collar placed inside an envelope (Example 10).

FIG. 2 shows the novel device of FIG. 1 from the same horizontal cut-away viewpoint, but not adjacent to collar 6, within a impermeable container or envelope 7, preferably of heat sealed aluminum, containing a predetermined amount of removable substance 2 so as to make a chemical equilibrium of said substance within and without said cavity "A". Hence, the novel device only becomes activated when envelope 7 is opened. The novel depletion indicator becomes activated only upon the desire of the user and generally when the pet collar is placed on the pet.

Figure 3:
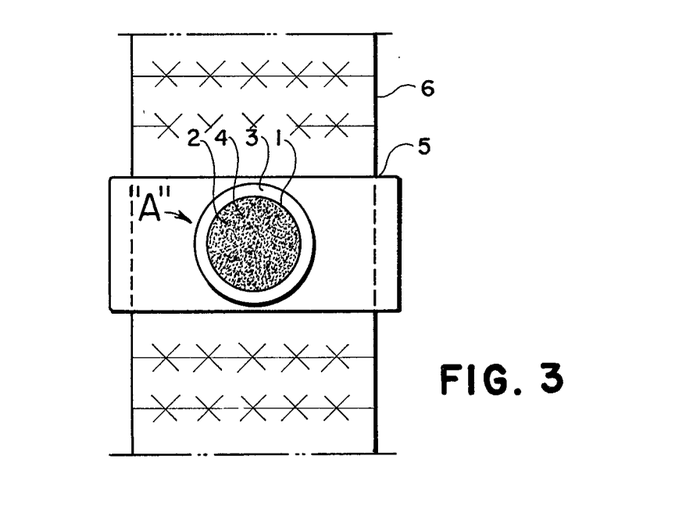
FIG. 3 shows the same embodiment as FIG. 1, except from the vertical along lines 3—3 of FIG. 1 (Example 10).

FIG. 3 shows the activated novel depletion indicator along lines 3—3 of FIG. 1, i.e., from the vertical.

EXAMPLE 11

Figure 4:
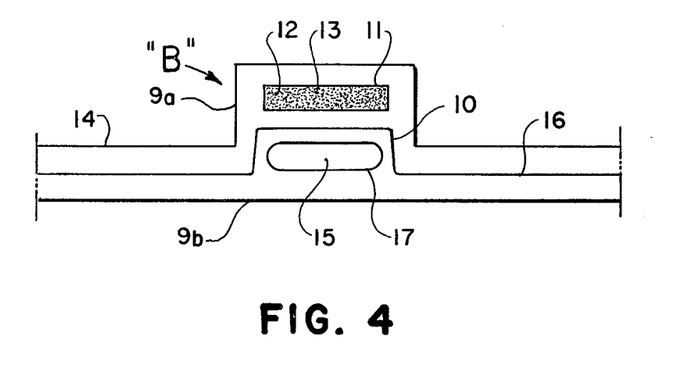
FIG. 4 shows an embodiment of the three component time watch of my invention from a horizontal cut-away viewpoint (Example 11).
Figure 5:
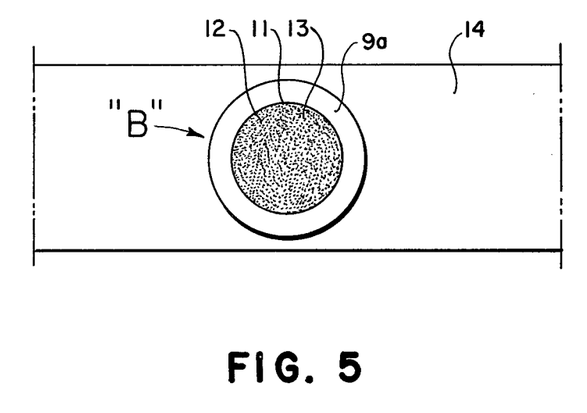
FIG. 5 shows the same embodiment of FIG. 1, except from the vertical along lines 4—4 of FIG. 4 (Example 11).

In FIG. 4, an embodiment for the 3-component novel time watch of the invention is shown: The embodiment takes the form of a cavity "B" protruding from band 14 which may be placed adjacent to a sterilized item or foodstuff (not shown) for which spoilage is to be indicated. Cavity "B" comprises impermeable film layers 9a and 9b, generally of 0.010 to 0.015 inch thicknesses and maybe of same substance used for the permeable film, e.g., polypropylene or polyvinylchloride. Layer 9a must be transparent, surrounding porous matrix 11 containing a suitable pH indicator 12 and an acid or base 13.

Pouch 17 is impermeable and crushable, i.e., upon crushing it releases a removable (or "controlled release") substance 15. If material 13 is an acid, the removable substance 15 is a base; if the material 13 is a base, the removable substance 15 is an acid. Pouch 17 and porous matrix 11 are separated by vapor permeable film 16 (of 0.001 to 0.005 inches, and thickness thereof generally about $\frac{1}{3}$ to about 1/5 the thickness of the impermeable film layers 9a and 9b), through which the removable substance may pass to reach the matrix 11 after the pouch 17 has been crushed. Film thickness 9a, 9b and 16 are dependent upon the time to be measured and the relative pressures on both sides of the permeable film. Pouch 17 has a thickness of 8 mils (0.16 to 0.2 mm) and is made of glass.

Other embodiments of the invention are readily apparent to those of ordinary skill in the art. The examples given previously are designed solely to aid the artisan in understanding the invention but many other configurations are possible and the invention is not intended to be limited to those working examples but only by the claims appended hereto.

If short periods of time are to be measured, acid or base 13 may be deleted depending upon the permeable film 16, pH color indicator 12, and concentration of removable substance 15 selected (see Example 9). It will also become apparent to one skilled in the art that in the two-component system of FIG. 1, the envelope 7 may be omitted for storage if a crushable pouch of the type shown in FIG. 4 (14) surrounds porous matrix 1.

It will be apparent to one skilled in the art that the matrix used for all embodiments of the invention may be omitted or may be replaced by a liquid containing the pH color indicator which is incapable of diffusing through the permeable film.

What is claimed is:

1. A device for indicating the depletion of a removable substance by observing a color change, said device comprising:
    (a) a permeable film; and
    (b) a porous matrix containing a mixture consisting essentially of (1) a predetermined amount of a removable substance (I) containing acidic or basic groups and (II) capable of diffusing through said permeable film (a) and (2) a pH color indicator that undergoes a color change at a predetermined pH range without a chemical reaction with (I) without a broader pH range, said broader pH range bounded by a first pH measurable at said predetermined amount corresponding to when said removable substance commences to diffuse through said permeable film (a) and a second pH measurable after said removable substance has diffused through said permeable film and said color has occurred, said permeable film (a) containing said porous matrix (b).

2. The device of claim 1 wherein said porous matrix is selected from the group consisting of cellulose, polystyrene, a tetrafluoroethylene polymer, and polyester.

3. The device of claim 1 wherein said removable substance is a pesticide.

4. The device of claim 1 wherein said removable substance is an insecticide.

5. The device of claim 1 wherein said pH color indicator is selected from the group consisting of methyl red, chlorophenol red, ethyl red, malachite green, and phenol red.

6. The device of claim 1 wherein said pH color indicator is selected from the group consisting of o-cresolphthalein, thymolphthalein, alizarin yellow and phenolphthalein.

7. The device of claim 1 wherein said permeable film is selected form the group consisting of polypropylene, polyethylene, polyvinylchloride, polycarbonate, polyester, and polyamide.

8. The device of claim 1 wherein said removable substance is ethylenediamine and said pH color indicator is phenolphthalein.

9. The device of claim 1 wherein said removable substance is 2,2-dichlorovinyl dimethyl phosphate and said pH color indicator is chlorophenol red.

10. The device of claim 1 wherein said removable substance is hydrochloric acid and said pH color indicator is methyl red.

11. The device of claim 1 wherein said permeable film is polypropylene.

12. The device of claim 1 wherein said permeable film is polyvinylchloride.

13. The device of claim 1 wherein said removable substance is dimethyl phosphite and said pH color indicator is chlorophenol red.

14. The device of claim 1 wherein said removable substance is hydrochloric acid and said pH color indicator is malachite green.

15. The device of claim 1 wherein said pH color indicator and said removable substance are initially present in a ratio of the former to the latter of about 1 $g/10^2$ ml to about 1 $g/10^6$ ml.

16. The device of claim 1, wherein an impermeable crushable pouch is within the permeable film, which pouch also contains the matrix.

17. The device of claim 1 further comprising
    an impermeable crushable pouch containing said porous matrix (b), said impermeable crushable pouch within said permeable film (a).

18. The device of claim 1 further comprising a color painted on said permeable film in an area adjacent said porous matrix (a) and having a color corresponding to that of said pH color indicator (2) after it has changed color.

19. The device of claim 18 further comprising a second color painted on said permeable film in the area adjacent said porous matrix (a) and having a color corresponding to that of said pH color indicator (2) after it has started but not yet completed its color change.

20. A time watch for determining when a predetermined period of time has elapsed by observing a color change, comprising:
    (a) a permeable film;
    (b) a porous matrix containing a mixture consisting essentially of (1) a controlled release substance having acidic or basic groups diffusable through said permeable film (a); and (2) a suitable pH color indicator that undergoes a color change without a chemical reaction with said controlled release substance (1) and in a predetermined pH range within a broader pH range bounded by:
        (aa) a pH of (a)(1) measurable before any migration of (b)(1) from the porous matrix and before any color change has occurred; and
        (bb) a pH of (a)(2) measurable after migration of (b)(1) from the porous matrix and after the color change has occurred;
    (c) an impermeable crushable pouch containing an acid or base having acidic or a basic groups with the proviso that if the controlled release substance of (b)(1) is an acid, the crushable pouch contains a base and if the controlled release substance is a base, the pouch contains an acid; and with a second proviso that said pouch and porous matrix are separated by said permeable film through which (b)(1) is diffusable; and (d) a transparent impermeable container containing (a), (b) and (c) by which the porous matrix can be observed.

21. A device for indicating the depletion of a controlled release substance by observing a color change comprising:

(A) a mixture consisting essentially of:
(1) a controlled release substance containing acid or basic groups;
(2) a suitable pH color indicator that undergoes a color change without a chemical reaction with said controlled release substance and at a pH within a pH range bounded by a first pH measured as the concentration of said controlled release substance starts to diminish in said device and a second pH measured after said controlled release substance has completely diminished; and (B) a permeable film containing said mixture, said film characterized by having the ability to pass said controlled release substance therethrough.

22. A time watch for determining when a predetermined period of time has elapsed by observing a color change, said time watch comprising:

(a) a permeable film;
(b) an impermeable crushable pouch containing a controlled release substance having acidic or basic groups and diffusable through said permeable film (a);
(c) a porous matrix containing a mixture consisting essentially of (1) an acid or a base and (2) a suitable pH color indicator that undergoes a color change without a chemical reaction with said controlled release substance and at a predetermined pH range within a broader pH range, said broader pH range bounded by (aa) a pH measurable before said controlled release substance initially contacts (c)(1) with the proviso that if the groups of said controlled release substance are acidic, then (c)(1) is a base and if the groups of said controlled release are basic, then (c)(1) is an acid and (bb) a second pH measurable after said controlled release substance has intimately contacted and has completely neutralized (c)(1) and said pH color indicator has completely changed color; said permeable film (a) separating said impermeable crushable pouch (b) and said porous matrix (c); and
(d) a transparent impermeable container containing (a), (b), and (c) permitting said porous matrix (c) to be observed.

23. The device of claim 22 wherein the pH color indicator is thymol blue and the release substance is hydrochloric acid.

24. A time watch for determining when a predetermined period of time has elapsed by observing a color change, said time watch comprising:

(a) a permeable film;
(b) a porous matrix containing a mixture consisting essentially of (1) a predetermined amount of a removable substance containing acidic or basic groups and capable of diffusing through said permeable film and (2) a suitable pH color indicator that undergoes a color change without a chemical reaction with said removable substances, and at a predetermined pH range within a broader pH range, said broader pH range being bounded by a first pH measurable at said predetermined amount when said removable substance commences to diffuse through said permeable film and a second pH measurable after said removable substance has diffused through said permeable film and the color change has occurred;

(c) an impermeable crushable pouch covering said permeable film and said porous matrix, with the proviso that said impermeable crushable pouch and said porous matrix are separated by said permeable film; and (d) a transparent impermeable container containing (a), (b), and (c) permitting said porous matrix (b) to be observed.

25. A method for indicating the depletion of a controlled release substance having a known period of effectiveness after activation of said controlled release substance, by a color change, said method comprising:

(a) activating the release of a removable substance through a permeable film, said removable substance being placed in a porous matrix containing a mixture consisting essentially of said removable substance and a suitable pH indicator, said removable substance being present in a predetermined amount, and capable of diffusing through said permeable film, and containing acidic or basic groups, said suitable pH color indicator capable of undergoing a color change without a chemical reaction with the removable substance and at a predetermined pH range within a broader pH range, said broader pH range being bounded by a pH measurable at said predetermined amount when said removable substance commences to diffuse through said permeable film and a second pH measurable after said removable substance has diffused through said permeable film and the color change has occurred, and (b) noting said color change.

26. The method of claim 25 wherein activation is accomplished by
tearing an impermeable pouch containing the removable substance in the same concentration as within said permeable film and porous matrix, which pouch is detachable from said permeable film.

27. The method of claim 25 wherein the removable substance is different from the controlled release substance and is non-toxic.

28. The method of claim 25 wherein the controlled release substance is a pesticide or insecticide in an animal collar.

29. The method of claim 28 wherein the activation set occurs substantially simultaneously with the activation of the animal collar.

30. A method for determining when a predetermined period of time has elapsed, comprising:
gently crushing the time watch of one of claims 20, 21 or 22 and crushable pouch therein.

* * * * *

UNITED STATES PATENT OFFICE
CERTIFICATE OF CORRECTION

Patent No. 4,248,597    Dated   February 3, 1981

Inventor(s)   Gerald W. McNEELY

It is certified that error appears in the above-identified patent and that said Letters Patent are hereby corrected as shown below:

On the front page of the patent (disclosing the inventor, assignee, Abstract, etc.) under "References Cited" correct the spelling of "Bruschi" opposite "[U.S. Pat.] 4,066,403  1/1978"; and "Khattab et al" opposite "[U.S. Pat.] 3,966,414".

On the same front page, under the Abstract, line 4, insert "," after "removable"; and line 5, delete "suitable" before "pH".

In Col. 6, line 11, insert a dash, "--", after "three".

In Col. 11, line 29(30?), change "14" to "17".

In Claim 1, Col. 11, line 48, after "(I)", change "without" to "within".

Signed and Sealed this

Fourteenth Day of July 1981

[SEAL]

Attest:

GERALD J. MOSSINGHOFF

Attesting Officer    Commissioner of Patents and Trademarks